(12) United States Patent
Luebke et al.

(10) Patent No.: US 10,392,330 B2
(45) Date of Patent: Aug. 27, 2019

(54) PROCESS FOR PRODUCING DIISOPROPYL ETHER FROM HIGH PURITY PROPYLENE

(71) Applicant: UOP LLC, Des Plaines, IL (US)

(72) Inventors: Charles P. Luebke, Mount Prospect, IL (US); Steven L. Krupa, Fox River Grove, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/824,993

(22) Filed: Nov. 28, 2017

(65) Prior Publication Data

US 2018/0179134 A1 Jun. 28, 2018

Related U.S. Application Data

(60) Provisional application No. 62/439,303, filed on Dec. 27, 2016.

(51) Int. Cl.
| | |
|---|---|
| C07C 41/06 | (2006.01) |
| C07C 41/36 | (2006.01) |
| C07C 43/04 | (2006.01) |
| B01J 31/08 | (2006.01) |
| B01D 3/14 | (2006.01) |
| B01D 3/36 | (2006.01) |
| C07C 41/05 | (2006.01) |
| C07C 29/04 | (2006.01) |

(52) U.S. Cl.
CPC .............. *C07C 41/06* (2013.01); *B01D 3/141* (2013.01); *B01D 3/36* (2013.01); *B01J 31/08* (2013.01); *C07C 29/04* (2013.01); *C07C 41/05* (2013.01); *C07C 41/36* (2013.01); *C07C 43/04* (2013.01)

(58) Field of Classification Search
CPC .......... C07C 41/06; C07C 41/36; B01J 31/08; B01D 3/14; B01D 3/36
See application file for complete search history.

(56) References Cited

U.S. PATENT DOCUMENTS

| | | | |
|---|---|---|---|
| 3,256,250 A | 6/1966 | Frilette | |
| 4,182,914 A | 1/1980 | Imaizumi | |
| 4,269,943 A | 5/1981 | Costin | |
| 4,705,808 A | 11/1987 | Brandes | |
| 4,935,552 A | 6/1990 | Child et al. | |
| 5,102,428 A | 4/1992 | Owen et al. | |
| 5,208,387 A | 5/1993 | Harandi et al. | |
| 5,324,865 A | 6/1994 | Beech et al. | |
| 5,324,866 A * | 6/1994 | Marker | C07C 29/04 568/697 |
| 5,371,301 A | 12/1994 | Marker et al. | |
| 5,473,105 A * | 12/1995 | Marker | C07C 41/06 568/671 |
| 5,504,257 A * | 4/1996 | Marker | C07C 41/05 568/694 |
| 5,600,023 A | 2/1997 | Marker et al. | |
| 5,744,645 A | 4/1998 | Marker et al. | |
| 5,986,148 A | 11/1999 | Beech et al. | |

FOREIGN PATENT DOCUMENTS

| | | |
|---|---|---|
| GB | 1176620 A | 1/1970 |
| WO | 9201661 A1 | 2/1992 |

OTHER PUBLICATIONS

Elvers et al., Ullmann's Encyclopedia of Industrial Chemistry, 5th ed. (1997); vol. A14, pp. 397-398.
PCT Search Report dated Mar. 29, 2018 for corresponding PCT Application No. PCT/US2017/066694.

* cited by examiner

*Primary Examiner* — Rosalynd A Keys

(57) ABSTRACT

A process for the production of diisopropyl ether from high purity propylene without the need of a propane-propylene fractionation column has been developed. The process involves (1) reacting a high purity propylene feedstock and water to produce isopropyl alcohol in a reactor and reacting the isopropyl alcohol with propylene to produce diisopropyl ether in the presence of an acidic ion exchange resin catalyst and a propane diluent to generate a reactor effluent stream containing at least water, isopropyl alcohol, diisopropyl ether, propylene, and acid, (2) passing the reactor effluent to an acid removal zone to produce an acid-depleted stream, (3) dividing the acid-depleted stream into two portions, (4) recycling a portion to the reactor (5) allowing propane to build-up to an amount sufficient to operate as a diluent and (6) recovering product diisopropyl alcohol.

4 Claims, 1 Drawing Sheet

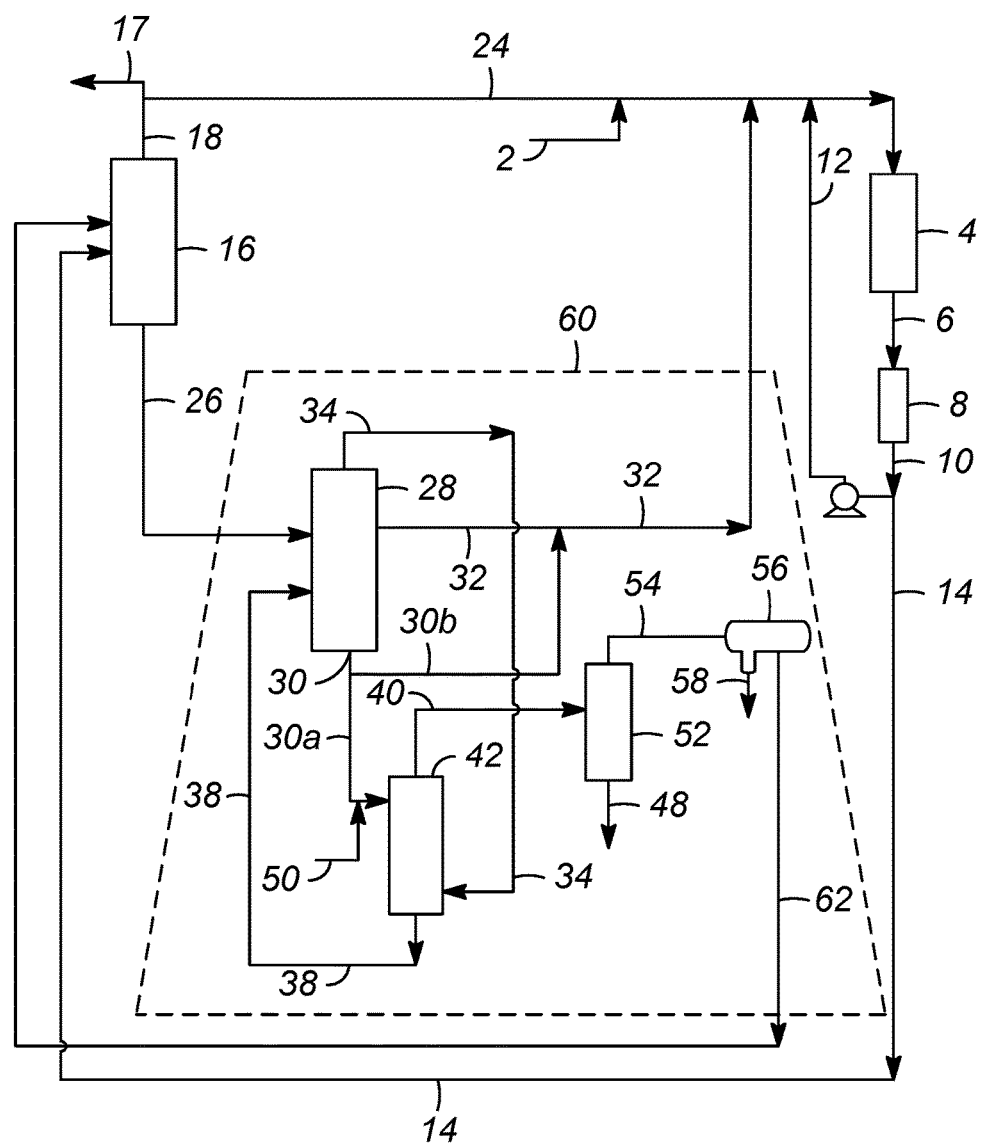

PROCESS FOR PRODUCING DIISOPROPYL ETHER FROM HIGH PURITY PROPYLENE

CROSS-REFERENCE TO RELATED APPLICATION

This application claims priority from Provisional Application No. 62/439,303 filed Dec. 27, 2016, the contents of which cited application are hereby incorporated by reference in its entirety.

BACKGROUND OF THE INVENTION

As tetraethyl lead is phased out, oxygenates have become more important in the petroleum refining industry as a source of gasoline octane boosters. The most common oxygenates for this purpose are the dialkyl ethers, especially those in the $C_5$ to $C_7$ range. One such dialkyl ether that is generating much interest is diisopropyl ether (DIPE). DIPE is in the boiling range of gasoline, has a high blending octane number, and one reactant generally used in the formation of DIPE, propylene, is a by-product commonly available in refineries. The preparation of DIPE from propylene proceeds by two sequential reactions, where propylene is first hydrated to isopropyl alcohol (IPA) (1) followed by reaction of the alcohol with the olefin (2) or by a single bimolecular dehydration reaction of the alcohol (3) (Williamson synthesis) according to the equations,

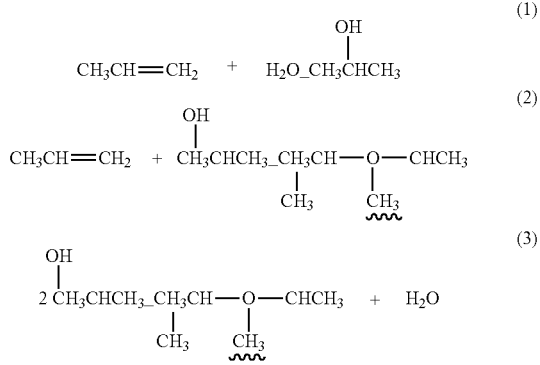

These reactions are catalyzed by a variety of catalysts such as activated charcoal, clays, resins, and zeolites. In particular, the reactions may be catalyzed by acidic ion exchange resins including sulfonated cation exchange resins such as sulfonated polystyrene resins and sulfonated styrene/divinylbenzene co-polymers as disclosed in U.S. Ser. No. 08/079,768, G.B. 1,176,620, and U.S. Pat. No. 4,182,914. Halogenated strong acid ion exchange resins such as those described in U.S. Pat. Nos. 4,705,808, 4,269,943, and 3,256,250 also may be used. A recognized problem of these catalysts is their susceptibility to hydrolysis of the acidic groups causing the transfer of acidic material from the catalysts into the reaction mixture and ultimately into the reactor effluent. The hydrolysis depends strongly on the reaction temperature, and the higher the temperature the greater the degree of hydrolysis. Steps may be taken to remove acid from process streams to protect downstream process units.

The propylene-containing hydrocarbon feedstock may be a refinery $C_3$ hydrocarbon stream and will most likely be a mixture of propylene and propane. Previously, the propylene-containing hydrocarbon feedstock typically contain at least about 50 mass-% propylene, or from about 70 to about 80 mass-% propylene. Sources for the propylene-containing hydrocarbon feedstock have included gas plant off-gas containing propylene, naphtha cracker off-gas containing light olefins, propylene from a propane dehydrogenation process, and refinery fluidized catalytic cracked (FCC) propane/propylene streams.

Recently, high purity propylene feedstocks have become available where the feedstock comprises from about 90 mass-% to about 99.9 mass-% propylene. Therefore there is a need for a process for generating dialkyl ethers using high purity propylene feedstocks.

SUMMARY OF THE INVENTION

The invention provides a process for producing diisopropyl ether from high purity propylene feedstocks comprising from about 90 mass-% to about 99.9 mass-% propylene and from about 0.1 to about 1 mass-% propane. The process of the invention involves (1) reacting, in a reactor and in the presence of an acidic ion exchange resin catalyst, the propylene of a high purity propylene feedstock and water to produce isopropyl alcohol and reacting the isopropyl alcohol with propylene to produce diisopropyl ether to afford a mixture containing at least water, isopropyl alcohol, diisopropyl ether, propylene, and acid; (2) passing the reactor effluent to an acid removal zone to produce an acid-depleted mixture; and (3) recycling a portion of the acid-depleted mixture to the reactor (4) passing a portion of the acid-depleted mixture to a light ends removal zone to separate unreacted propylene and propane from the reaction products and water and (5) purging a portion of the propane and recycling propylene to the reactor.

The light ends removal zone also provides a water, isopropyl alcohol, and diisopropyl ether enriched stream. Diisopropyl ether is recovered from a portion of the acid-depleted stream through the generation of the water, isopropyl alcohol, and diisopropyl ether enriched stream and then passing the stream to a separation zone to afford a water stream, an isopropyl alcohol-water azeotrope stream, and a diisopropyl ether-isopropyl alcohol-water azeotrope stream; passing the water stream to a water wash zone, the isopropyl alcohol-water azeotrope stream to the reactor, and the diisopropyl ether-isopropyl alcohol-water azeotrope stream to a settler to afford a diisopropyl ether enriched stream and a water enriched stream; and passing the diisopropyl ether enriched stream to the water wash zone to afford an isopropyl alcohol and water stream which is passed to the second separation zone, and a diisopropyl ether product stream containing at least 96 mass-% diisopropyl ether.

BRIEF DESCRIPTION OF THE DRAWING

The FIGURE is a schematic representation of the preferred embodiment of the invention.

DETAILED DESCRIPTION OF THE INVENTION

The invention applies to single stage DIPE production processes where the hydration of propylene to form IPA and the etherification of IPA and propylene to form DIPE are performed concurrently using an acidic ion exchange resin to catalyze both reactions, while protecting the reaction catalyst and downstream zones from degradation due to the introduction of acid. The invention further provides a DIPE production process which does not require breaking the IPA-water azeotrope which is formed in the process.

The process of the invention begins with introducing water and a hydrocarbon feedstock containing propylene to a reactor containing an acidic ion exchange resin catalyst. The operating conditions of the reactor include pressures of about 100 to about 1500 psia, or from about 700 to about 1000 psia, and temperatures of about 105 to about 133° C., or from about 108 to about 130° C. or from about 108 to about 125° C. It is common to slowly increase the operating temperature as the catalyst ages. Suitable water to olefin mole ratios include from about 0.1:1 to about 0.8:1, or about 0.5:1. Greater water to olefin mole ratios may be used, but the invention would become less economically attractive, as discussed below. The propylene-containing hydrocarbon feedstock may be a refinery $C_3$ hydrocarbon stream and will most likely be a mixture of propylene and propane. The propylene-containing hydrocarbon feedstock should contain at least about 90 mass-% propylene, or from about 90 to about 99 mass-% propylene, or from about 90 to about 99.9 mass-%. Suitable sources for the propylene-containing hydrocarbon feedstock include, but are not limited to, gas plant off-gas containing propylene, naphtha cracker off-gas containing light olefins, propylene from a propane dehydrogenation process, and refinery fluidized catalytic cracked (FCC) propane/propylene streams or high purity propylene from other sources.

A diluent of $C_4$ may be added to a system to produce DIPE. The diluent may be a closed loop diluent, it is not reactive and merely circulates. The diluent provides dilution of the reactants to control the temperature in the reactor and minimize an exotherm. The diluent may be added at start-up of the process, and additional diluent may be added if needed. The $C_4$ may be isobutane or normal butane or mixtures thereof. $C_4$ diluent is particularly advantageous since $C_4$s do not form azeotropes with the oxygenate byproducts.

However, it has been found that an external diluent such as $C_4$ is not required. Applicants have found that the existing propane that is introduced with the feedstock may be allowed to build up in the system so that it functions as the diluent. In this way, additional material need not be acquired to function as the diluent. No further diluent beyond the propane in the feedstock is required. After the propane has built to a concentration sufficient to serve as a diluent, a purge may be employed to control the concentration of propane.

The acidic ion exchange resin catalysts may be any of those commonly used for a DIPE production process including sulfonated cation exchange resins such as sulfonated polystyrene resins and sulfonated styrene/divinylbenzene co-polymers. An example of a suitable sulfonated styrene/divinylbenzene co-polymer catalyst is Purolite CT-175 sold by Purolite. These sulfonated cation exchange resins are common in the art and do not require discussion here. For reference, see, U.S. Ser. No. 08/079,768, G.B. 1,176,620, and U.S. Pat. No. 4,182,914. Halogenated strong acid ion exchange resins such as those described in U.S. Pat. Nos. 4,705,808, 4,269,943, and 3,256,250 may also be used.

As the propylene and water contact the catalyst, the hydration reaction (1) takes place and IPA is formed. As the IPA and propylene contact the catalyst, the etherification reaction (2) takes place and DIPE is formed. Reaction (3) may also take place to form DIPE, but it is less preferred due to the increased consumption of IPA as compared to reaction (2). The reactor may be a single bed reactor or may contain two or more beds with interstage cooling. Propane is not reacted.

During operation, some of the acid from the catalyst will enter into the reaction mixture. For example, the reactor effluent may contain from as little as 1 to greater than 100 mass ppm of oxo acids of sulfur with a typical value of about 1 to about 20 mass ppm, and/or as little as 1 to greater than 100 mass ppm chloride with a typical value of about 1 to about 20 mass ppm depending upon the catalyst composition and the age of the catalyst. It is common practice to recycle a portion of the reactor effluent in order to increase conversion of propylene and IPA to DIPE and to control the temperature in the reactor. However, when the acid is not removed from the reactor effluent, and a portion of the reactor effluent is recycled to the reactor, the catalyst is rapidly deactivated. When the acid is removed from the reactor effluent prior to recycling, the life of the catalyst is significantly extended. Therefore the entire reactor effluent may be introduced to an acid removal zone prior to recycling.

The acid removal zone contains any solid particles capable of removing the acid from the reactor effluent. For example, the solid particles may be alkaline metal oxides, base ion exchange resins, basic organically-bridged polysilsesquioxanes particles, or activated carbon, or any other strongly basic inorganic compounds with reasonable thermal stability considering the reactor effluent will be at temperatures from about 105 to about 133° C. Examples of suitable base ion exchange resins include strong base quaternary ammonium anion exchangers, amine-type weak base anion exchangers, or pyridine-type anion exchangers. Specific suitable commercial base ion exchange resins include Amberlite® IRA-67, Amberlite® IRA-68, Amberlite® IRA-93, Amberlite® CG-420, Amberlite® IRA-410, Amberlite® IRA-900, Amberlite® IRA-904, Duolite A-7, Duolite A-368, Amberlyst A-21, Amberlyst A-26, Amberlyst A-27, Dowex® 1X2-100, Dowex® 1X2-200, Dowex® 1X2-400, Dowex® 1X8-50, Dowex® 1X8-100, Dowex® 1X8-200, and Dowex® 1X8-400 which are sold by companies such as Rohm and Haas, Diamond Shamrock, or Dow. The more preferred resins are those that are stable at higher temperatures such as Amberlite® IRA-67 and Amberlite® IRA-68. These types of base ion exchange resins are readily commercially available and are very well known in the art and do not require discussion here. See generally, *Ullmann's Encyclopedia of Industrial Chemistry,* 5th ed.; Elvers, B., Hawkins, S., Ravenscroft, M., Schulz, G., Eds.; Wienham: Cambridge, N.Y., Vol. A14, pp. 397-398. The base ion exchange resins may be regenerated for reuse, and typically a process would contain two interchangeable base ion exchange chambers so that one chamber is in use while the base ion exchange material in the other chamber is being regenerated.

When using the base ion exchange resins, it is important to observe the thermal limitations of the resins. Most resins are stable at temperatures from ambient to a maximum of about 100° C. with a few being stable at up to 108° C. It is advantageous to operate the reactor so that the reactor effluent will be at a temperature within the stable temperature range of the resins so that heat exchangers would not be required to lower the temperature of the reactor effluent before entering the acid removal zone. Suitable basic organically-bridged polysilsesquioxanes are any which are capable of removing acid from the reactor effluent. Examples of basic organically-bridged polysilsesquioxanes that are appropriate for use in the acid removal zone include those having a divalent radical whose parent is selected from the group consisting of dipropylamine, dipropylphenylamine, tripropylamine, and diphenylamine.

As the reactor effluent is introduced to the acid removal zone, the acid contacts the base ion exchange resin and is exchanged with the basic group of the resin and is no longer carried with the fluid flow. Alternatively, the acid contacts the basic organically-bridged polysilsesquioxane and is removed from the fluid flow. The stream exiting the acid removal zone is acid-depleted and has an oxo acids of sulfur concentration, or an oxo acids of sulfur and chloride concentration sum of less than 0.1 mass ppm. At least a portion of the acid-depleted stream is recycled to the reactor to react the propylene and IPA to form DIPE and to control the temperature in the reactor. Suitable recycle ratios range from about 2:1 to about 10:1 or 5:1. At least a portion of the acid-depleted stream containing water, IPA, DIPE, propylene, and propane, is passed to downstream processing zones to recover product DIPE. One possible downstream processing flowscheme which has the advantage of not requiring equipment to break the IPA-water azeotrope is as follows.

A portion of the acid-depleted stream is passed to a light ends fractionation zone for removal of compounds such as propylene and propane. The light ends fractionation zone may be operated at a temperature of about 80° C. and a pressure of about 235 psig.

In other processes, it is common for the light compounds such as propylene and propane to be passed to a propylene/propane fractionation column where propane and propylene are separated into two streams. The propane enriched stream would be collected, and the propylene enriched stream would be recycled to the reactor. The recycle may be combined with the seed stock or may be used as an interstage quench. The heavier compounds such as water, IPA, and DIPE are passed to a water-IPA-DIPE splitter column.

With the feed here being high purity propylene, the propylene/propane fractionation column of traditional flow schemes is not necessary thereby saving large capital and operational costs.

Instead, a stream of propane and propylene is taken as an overhead stream from the light ends fractionation column. As the concentration of propane in the overhead stream is very small due to the feedstock being a high purity propylene feedstock, no propylene/propane fractionation column is required. Furthermore, the unreacted propane is used as the diluent to minimize the exotherm in the reactor. Since propane is part of the feedstock, albeit a small concentration, and it is not reacted, the propane is allowed to build up in the system until reaching a sufficient concentration to operate as the diluent. After reaching the desired concentration, a small purge stream may be taken from the overheard stream so that the concentration of propane does not exceed the amount required as a diluent. The rest of the overhead stream is passed to the reactor for reaction of the propylene.

As discussed above, at least a portion of the acid-depleted stream is recycled to the reactor to react the propylene and IPA to form DIPE and to control the temperature in the reactor. The remaining portion of the acid-depleted stream is passed to the light ends fractionation zone, where the bottoms product from the light ends fractionation zone is further passed to the water-IPA-DIPE splitter column which is a fractionation column operating at from about 65 to about 100° C. and from about 5 to about 25 psig that separates the heavier compounds into a DIPE-IPA-water azeotrope stream, the water into another stream, and an IPA-water azeotrope into a yet another stream. The water stream is passed to a water wash zone, discussed below, and the DIPE-IPA-water azeotrope stream is passed to a settler. The IPA-water azeotrope stream is recycled to the reactor without breaking the azeotrope which is a significant cost savings since, in order to break the azeotrope, another process unit would be required.

In the settler, the DIPE-IPA-water azeotrope forms two phases, a DIPE enriched phase of about 95 mass-% DIPE, about 1 mass-% water, and about 4 mass-% IPA, and a water enriched phase of about 94 mass-% water, about 1 mass-% DIPE, and about 5 mass-% IPA. The water enriched phase is recycled either directly to the water-IPA-DIPE splitter, or is combined with the IPA and water stream exiting the water wash zone; see below. The DIPE enriched phase is passed to a water wash zone.

The water wash zone is operated at from about 10 to about 66° C. and from about 1 to about 10 psig. The DIPE enriched phase and a water stream, which includes the water stream from the water-IPA-DIPE splitter, are introduced to the water wash zone in a ratio of about 1:5 to about 1:10 to form an IPA and water stream which is recycled to the water-IPA-DIPE splitter, and a DIPE stream, containing at least 96 mass-% DIPE, which is collected.

Without intending any limitation of the scope of the present invention and as merely illustrative, the invention is explained below in specific terms as applied to a specific embodiment of the invention which is based on a design for a commercial scale unit. Referring to the FIGURE, a 99 mass-% propylene-1 mass-% propane feed 2 water, IPA, propylene, propane, and DIPE containing recycle 12, IPA-water azeotrope containing stream 32, and propylene and propane-containing recycle 24 are combined and introduced to hydration and etherification reactor 4 which contains sulfonated styrene/divinylbenzene co-polymer ion exchange resin catalyst. Reactor 4 is operated at 110° C. and 1000 psig. In reactor 4, the hydrolysis of propylene is catalyzed and IPA is formed, the IPA is then catalytically reacted with propylene to form DIPE. Some $SO_3$ will to split off from the sulfonated styrene/divinylbenzene co-polymer ion exchange resin catalyst. The $SO_3$ is then hydrolyzed to form $H_2SO_4$ which is carried into the reaction mixture. Other oxo acids of sulfur such as $HSO_3^-$ or $HSO_4^-$ may be formed, but for ease of understanding, only $H_2SO_4$ will be discussed. The reactor effluent 6 contains propylene, propane, water, IPA, DIPE, and $H_2SO_4$, and is passed to acid removal unit 8 which contains Amberlite® IRA-68 base ion exchange resin. Acid removal unit 8 is operated at 80° C. and 975 psig. As the fluid reactor effluent 6 contacts the Amberlite® IRA-68 base ion exchange resin, $SO_4^-$ or $HSO_4^-$ from the reactor effluent is exchanged for $OH^-$ or 2 $OH^-$ from the resin, which neutralizes the $H^+$ thereby resulting in an $H_2SO_4$-depleted stream 10. The $H_2SO_4$-depleted stream 10 is divided into two portions, one portion, stream 12, is recycled to reactor 4, and one portion, stream 14, is passed to a light ends recovery unit 16. The recycle to feed rate is about 5:1. Fractionation in light ends recovery unit 16 at 80° C. and 235 psig results in an overhead propane and propylene stream 18, and a bottoms water, IPA and DIPE stream 26 which is passed to a recovery zone 60, and specifically a water-IPA-DIPE splitter column 28 of the recovery zone. After a period of time during which the propane concentration has grown to an amount sufficient to operate as a diluent, a purge stream 17 is removed from overhead propane and propylene stream 18 and the remainder 24 is passed to reactor 4. The purge stream prevents build-up of propane which is not consumed in the reactions of reactor 4.

In water-IPA-DIPE splitter column 28 the water, IPA and DIPE stream 26 is fractionated to form a water stream 30, a water-IPA azeotrope stream 32, and a DIPE-IPA-water azeotrope stream 34. Water-IPA azeotrope stream 32 is recycled to reactor 4, and a first portion of water stream 30a is recycled to a water wash unit 42 while a second portion of water stream 30b may be recycled to reactor 4. DIPE-IPA-water azeotrope stream 34 is passed to water wash unit 42 where the azeotrope is separated into a second water-IPA azeotrope stream 38 and a DIPE rich stream 40. DIPE rich stream 40 is passed to drying column 52. A DIPE product stream 48 containing at least 96 mass-% DIPE is withdrawn from drying column 52 and collected. A drying column overhead stream 54 is withdrawn from drying column 52 and passed to unit 56. A water stream 58 is removed from unit 56 and the remainder in stream 62 is recycled to light ends recovery unit 16. Water feed 50 may be used to add additional water to the system if necessary.

Specific Embodiments

While the following is described in conjunction with specific embodiments, it will be understood that this description is intended to illustrate and not limit the scope of the preceding description and the appended claims.

A first embodiment of the invention is a process for producing diisopropyl ether comprising (a) reacting water and the propylene of a feedstock containing at least 90 mass-% propylene and the balance propane, to produce isopropyl alcohol and reacting the isopropyl alcohol with propylene to produce diisopropyl ether in a reactor without an external diluent and in the presence of an acidic ion exchange resin catalyst at a temperature of from about 105° C. to about 133° C. to generate a reactor effluent comprising water, isopropyl alcohol, diisopropyl ether, propylene, propane and acid; (b) treating the mixture in an acid removal zone to generate an acid-depleted mixture; (c) recycling a portion of the acid-depleted mixture to the reactor, and passing a second portion of the acid-depleted mixture to a light ends fractionation column; (d) separating, in the light ends fractionation column, an overhead stream comprising propane and propylene, and a bottoms stream comprising water, isopropyl alcohol, and diisopropyl ether; (e) passing the overhead stream to the reactor until the concentration of propane is sufficient to operate as a diluent and then purging a portion of the overhead stream and passing the remainder of the overhead stream to the reactor; and (f) passing the bottoms stream to a recovery zone to separate and collect the diisopropylether. An embodiment of the invention is one, any or all of prior embodiments in this paragraph up through the first embodiment in this paragraph wherein the reactor comprises at least two beds with interstage cooling. An embodiment of the invention is one, any or all of prior embodiments in this paragraph up through the first embodiment in this paragraph wherein a portion of the acid-depleted mixture is recycled to the reactor at a location between beds to provide the interstage cooling. An embodiment of the invention is one, any or all of prior embodiments in this paragraph up through the first embodiment in this paragraph wherein the feedstock contains at least 99.9 mass-% propylene. An embodiment of the invention is one, any or all of prior embodiments in this paragraph up through the first embodiment in this paragraph further comprising in the recovery zone (g) passing the second portion of the acid-depleted mixture to a water-IPA-DIPE-splitter column to afford a water enriched mixture, an isopropyl alcohol-water azeotrope mixture, and a diisopropyl ether-isopropyl alcohol-water azeotrope mixture; (h) passing the isopropyl alcohol-water azeotrope mixture to the reactor; (i) passing the water mixture and the diisopropyl ether-isopropyl alcohol-water azeotrope mixture to the water wash zone to afford a diisopropyl ether enriched mixture, and a water and isopropyl alcohol enriched mixture; (j) recycling the water and isopropyl alcohol enriched mixture to the water-IPA-DIPE-splitter column; and (k) passing the diisopropyl ether enriched mixture to a drying column to generate product diisopropyl ether containing at least 96 mass-% diisopropyl ether.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for producing diisopropyl ether comprising:
(a) reacting water and the propylene of a feedstock containing at least 99.9 mass-% propylene and the balance propane, to produce isopropyl alcohol and reacting the isopropyl alcohol with propylene to produce diisopropyl ether in a single reactor without an external diluent and in the presence of an acidic ion exchange resin catalyst at a temperature of from about 105° C. to about 133° C. to generate a reactor effluent comprising water, isopropyl alcohol, diisopropyl ether, propylene, propane and acid;
(b) treating the mixture in an acid removal zone to generate an acid-depleted mixture;
(c) recycling a portion of the acid-depleted mixture to the reactor, and passing a second portion of the acid-depleted mixture to a light ends fractionation column;
(d) separating, in the light ends fractionation column, an overhead stream comprising propane and propylene, and a bottoms stream comprising water, isopropyl alcohol, and diisopropyl ether;
(e) passing the overhead stream to the reactor until the concentration of propane is sufficient to operate as a diluent and then purging a portion of the overhead stream and passing the remainder of the overhead stream to the reactor; and
(f) passing the bottoms stream to a recovery zone to separate and collect the diisopropylether.

2. The process of claim 1 wherein the reactor comprises at least two beds with interstage cooling.

3. The process of claim 1 wherein a portion of the acid-depleted mixture is recycled to the reactor at a location between beds to provide the interstage cooling.

4. The process of claim 1 further comprising in the recovery zone:
(g) passing at least a portion of the bottoms stream from the light ends fraction zone to a water-IPA-DIPE-splitter column to afford a water enriched mixture, an isopropyl alcohol-water azeotrope mixture, and a diisopropyl ether-isopropyl alcohol-water azeotrope mixture;
(h) passing the isopropyl alcohol-water azeotrope mixture to the reactor;

(i) passing the water mixture and the diisopropyl ether-isopropyl alcohol-water azeotrope mixture to the water wash zone to afford a diisopropyl ether enriched mixture, and a water and isopropyl alcohol enriched mixture;
(j) recycling the water and isopropyl alcohol enriched mixture to the water-IPA-DIPE-splitter column; and
(k) passing the diisopropyl ether enriched mixture to a drying column to generate product diisopropyl ether containing at least 96 mass-% diisopropyl.

* * * * *